United States Patent
Güven

(10) Patent No.: US 10,307,171 B2
(45) Date of Patent: Jun. 4, 2019

(54) HIGH TIBIAL OSTEOTOMY EXTERNAL FIXATOR

(71) Applicants: Melih Güven, Caddebostan, Kadiköy, Istanbul (TR); TST RAKOR VE TIBBi ALETLER SANAYi VE TiCARET LiMiTED SiRKETi, Kurtköy, Pendik, Istanbul (TR)

(72) Inventor: Melih Güven, Istanbul (TR)

( * ) Notice: Subject to any disclaimer, the term of this patent is extended or adjusted under 35 U.S.C. 154(b) by 83 days.

(21) Appl. No.: 15/519,564

(22) PCT Filed: Nov. 3, 2015

(86) PCT No.: PCT/TR2015/050157
§ 371 (c)(1),
(2) Date: Apr. 17, 2017

(87) PCT Pub. No.: WO2016/072954
PCT Pub. Date: May 12, 2016

(65) Prior Publication Data
US 2017/0238944 A1    Aug. 24, 2017

(30) Foreign Application Priority Data
Nov. 4, 2014   (TR) .................................. 201412961

(51) Int. Cl.
*A61B 17/64* (2006.01)
*A61B 17/16* (2006.01)
(Continued)

(52) U.S. Cl.
CPC ........ *A61B 17/1675* (2013.01); *A61B 17/152* (2013.01); *A61B 17/1764* (2013.01);
(Continued)

(58) Field of Classification Search
CPC ..... A61B 17/62; A61B 17/66; A61B 17/8095; A61B 17/8863; A61B 17/157;
(Continued)

(56) References Cited

U.S. PATENT DOCUMENTS 4,349,018 A * 9/1982 Chambers .............. A61B 17/15 30/293
4,750,481 A * 6/1988 Reese .................. A61B 17/152 606/87

(Continued)

FOREIGN PATENT DOCUMENTS

EP    1136041 A2 *  9/2001  .......... A61B 17/152
FR    2679126       1/1993
WO    2014057190 A1  4/2014

*Primary Examiner* — Eduardo C Robert
*Assistant Examiner* — Michelle C Eckman

(57) ABSTRACT

The invention is related with an external fixator that is used in High Tibial Osteotomy (HTO) surgeries, including at least one positioner (1) for gripping the leg from both sides, at least one angulation device (3) and a proximal arch (8) that is connected to the positioner (1), at least one proximal schanz holder (7) on the proximal arch (8), at least one distal schanz holder (4) at the bottom of the angulation device (3), at least one osteotomy block (5) that enables to set the size and the location of the incision on the proximal arch (8), at least one fibular head positioning device (2) that is connected to the angulation device (3) and at least one angular indicator (scale) (19) on the fixator, on which the correction can be adjusted and controlled.

14 Claims, 6 Drawing Sheets

(51) Int. Cl.
 *A61B 17/15* (2006.01)
 *A61B 17/17* (2006.01)
 *A61B 17/60* (2006.01)
 *A61B 17/84* (2006.01)
(52) U.S. Cl.
 CPC ............ *A61B 17/60* (2013.01); *A61B 17/842* (2013.01); *A61B 17/848* (2013.01)
(58) Field of Classification Search
 CPC ... A61B 17/1739; A61B 17/15; A61B 17/152; A61B 17/151; A61B 17/64
 See application file for complete search history.

(56) References Cited

U.S. PATENT DOCUMENTS

| | | | | |
|---|---|---|---|---|
| 5,364,402 A * | 11/1994 | Mumme | ............... | A61B 17/157 606/88 |
| 5,681,320 A | 10/1997 | McGuire | | |
| 7,794,467 B2 * | 9/2010 | McGinley | ........... | A61B 17/155 606/88 |
| 7,967,822 B2 * | 6/2011 | Haines | ................. | A61B 17/155 606/82 |
| 2005/0075641 A1 * | 4/2005 | Singhatat | ................ | A61B 17/15 606/86 R |
| 2008/0140213 A1 * | 6/2008 | Ammann | ................ | A61B 17/15 623/20.32 |
| 2008/0147073 A1 * | 6/2008 | Ammann | ................ | A61B 17/15 606/87 |
| 2008/0167654 A1 * | 7/2008 | Novak | ................. | A61B 17/151 606/88 |
| 2008/0188852 A1 | 8/2008 | Matityahu | | |
| 2010/0087824 A1 * | 4/2010 | Collazo | ................ | A61B 17/151 606/88 |
| 2010/0145345 A1 * | 6/2010 | Ammann | ............. | A61B 17/151 606/88 |
| 2011/0034963 A1 * | 2/2011 | Bagnasco | ............... | A61B 17/62 606/86 R |
| 2011/0125200 A1 * | 5/2011 | Hanson | ............... | A61B 17/1764 606/86 R |
| 2011/0125201 A1 * | 5/2011 | Hanson | ............... | A61B 17/1764 606/86 R |
| 2011/0213376 A1 * | 9/2011 | Maxson | ............... | A61B 17/151 606/88 |
| 2011/0218540 A1 * | 9/2011 | Ammann | ................ | A61B 17/15 606/87 |
| 2012/0215225 A1 * | 8/2012 | Philippon | ............... | A61B 17/15 606/87 |
| 2014/0074101 A1 | 3/2014 | Collazo | | |
| 2014/0074117 A1 * | 3/2014 | Hanson | ............... | A61M 5/3287 606/130 |
| 2014/0228852 A1 * | 8/2014 | Sasing | .................. | A61F 2/3859 606/88 |
| 2014/0288562 A1 * | 9/2014 | Von Zabern | ......... | A61B 17/151 606/88 |
| 2015/0157339 A1 * | 6/2015 | McGinley | .......... | A61B 17/1739 606/87 |
| 2015/0157340 A1 * | 6/2015 | McGinley | .......... | A61B 17/1739 606/87 |
| 2015/0238202 A1 * | 8/2015 | Collins | ................. | A61B 17/155 606/88 |
| 2015/0289910 A1 * | 10/2015 | Mirghasemi | ....... | A61B 17/8014 606/71 |
| 2016/0030028 A1 * | 2/2016 | Van Dyke | ............ | A61B 17/025 606/90 |
| 2016/0038185 A1 * | 2/2016 | Disegi | ................ | A61B 17/6416 606/59 |
| 2016/0135825 A1 * | 5/2016 | Toler | .................... | A61B 17/025 606/88 |
| 2017/0165142 A1 * | 6/2017 | Gockertiz | .............. | A61B 34/70 |
| 2017/0360473 A1 * | 12/2017 | Hanson | .............. | A61B 17/1764 |

\* cited by examiner

HIGH TIBIAL OSTEOTOMY EXTERNAL FIXATOR

CROSS REFERENCE TO RELATED APPLICATIONS

This is a National Stage of International Application No. PCT/TR2015/050157, filed Nov. 3, 2015, which claims the priority of Turkish Application No. 2014/12961, filed Nov. 4, 2014, the entire disclosures of which are hereby incorporated by reference in their entirety.

BACKGROUND OF THE INVENTION

1. Field of the Invention

The current invention is about fixators which are used in High Tibial Osteotomy (HTO) surgeries. The invention is especially related with a new High Tibial Osteotomy (HTO) external fixator that shortens the operation time and makes the surgery easier for the surgeon.

2. Description of the Prior Art

It is a pathology that is accelerating the gonarthrosis development when the mechanical axis alignment of the lower extremity is in varus position and narrowing of the medial knee joint space.

The High Tibial Osteotomy application from the proximal of the Tibia achieve the neutral position (neutral alignment: the mechanical axis alignment of the lower extremity passing through the middle of the knee joint or maximum 8 mm from the medial) of the mechanical axis and stops the gonoarthrosis process or slows it down.

HTO (High Tibial Osteotomy) applications can be accomplished from lateral as closed wedge, from medial open wedge or as dome osteotomies. Different implants (plate, staple, circular or uniplaner fixator etc.) are used at all these osteotomy choices.

At the open surgery applications from medial or lateral some problems like infection or nonunion can be seen. In addition some troubles could be seen at the stability which the fixation material provides.

Sometimes correction loss could be seen during the osteotomy when the opposite cortex breaks. After not stable fixation weight bearing cannot be given so the rehabilitation period of the patient is prolonged besides the healing time is prolonged too. At the big incision surgeries infection can occur because of the big incision. A solution is need that resolves this kind of problems and that helps the patient to heal soon.

SUMMARY OF THE INVENTION

According to the way of the technique the aim of the invention is to create a high tibial osteotomy (HTO) external fixator that eliminates the explained negativities.

Another purpose is graduated correction during the surgery with the HTO external fixation which is designed for open wedge osteotomy application from the medial, the patient is mobilized the day after surgery by weight bearing and if necessary changing of the correction amount in early period after the surgery can be accomplished, like these it has important advantages.

Another object of the invention is to reduce the operation time with the easy fixation to tibia.

Another object of the invention is different than plate and nail implantation, the determination of the osteotomy (bone cutting) is done after the fixation of the fixator.

It is another object of the present invention, with a 3-4 cm skin incision the osteotomy is applied without performing wide soft tissue dissection to reduce the surgical incision and to avoid the problems associated with the skin.

Another object of the present invention, during and after osteotomy, to apply a gradual and controlled distraction at the osteotomy line (the angular correction goals by performing the opening operation after cutting of the bone).

Another object of the invention to prevent the uncontrolled breakage of the osteotomy (the lateral cortex osteotomy or extend into the tibial plateau) line; even if breakage occurs, the installation allows early weight bearing due to the stability of the system.

Another object of the invention is to remove the system without the need for a second surgical procedure after obtaining the union at the osteotomy site. Especially in plate implantation the implant is removed with a second surgery, owing to the invention the fixator application can be removed without anesthesia in the operating room or in polyclinic conditions.

It is another object of the present invention, is to avoid the problems associated with the initiative skin incision which can be experienced in open surgery in knee replacement surgery which could be done after HTO (high tibial osteotomy). The incision which is used in Standard plate implantation and the incision for the knee prosthesis which is done later could intersect. In the fixator fixation a very small incision is used which does not prevent the incision of the knee prosthesis which will be done later on.

To achieve the purpose, to shorten the healing period of the patient and to increase the success of the surgical operation a new high tibial osteotomy (HTO) external fixator (high tibial osteotomy (HTO) externally fixation System) has been developed.

DESCRIPTION OF THE REFERENCE NUMERALS

Figure 1:
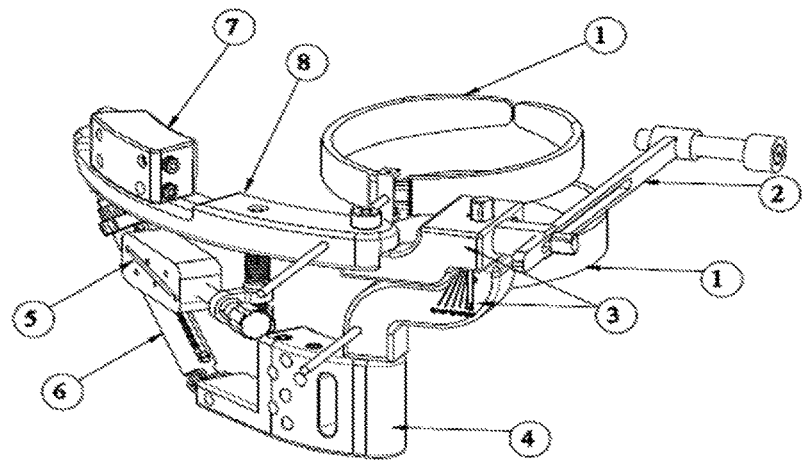
FIG. 1, A representative application of the invention is a drawing of the mounted state.
Figure 2:
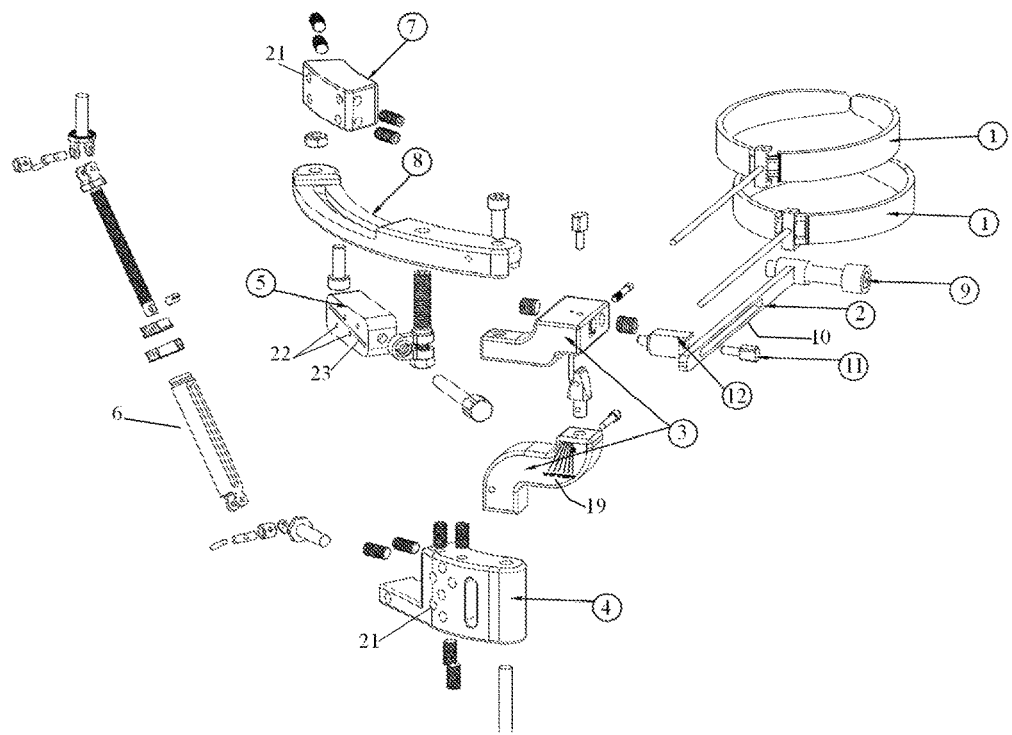
FIG. 2, A representative application of the invention is a drawing of the de-mounted state.
Figure 3:
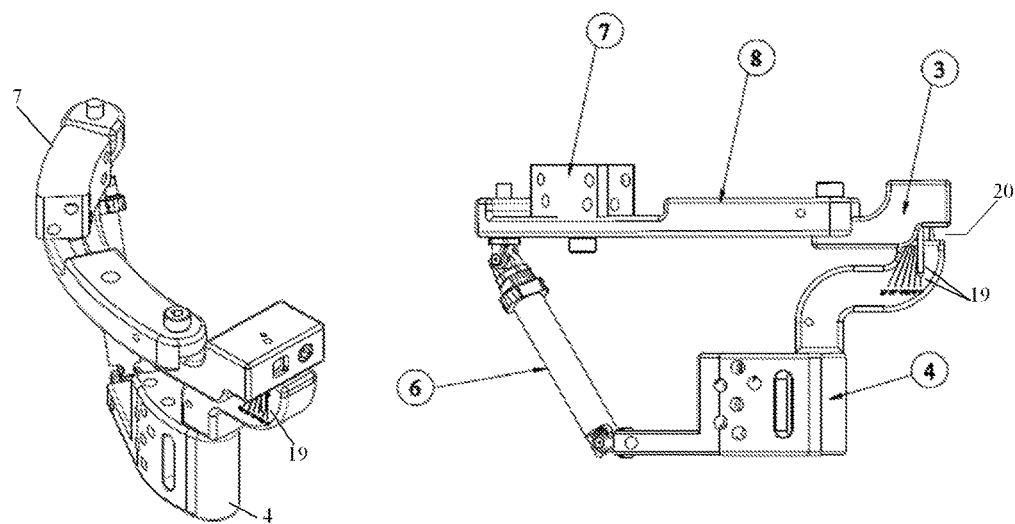
FIG. 3; A representative application of the invention is a drawing of a side and a side perspective view.
Figure 4:
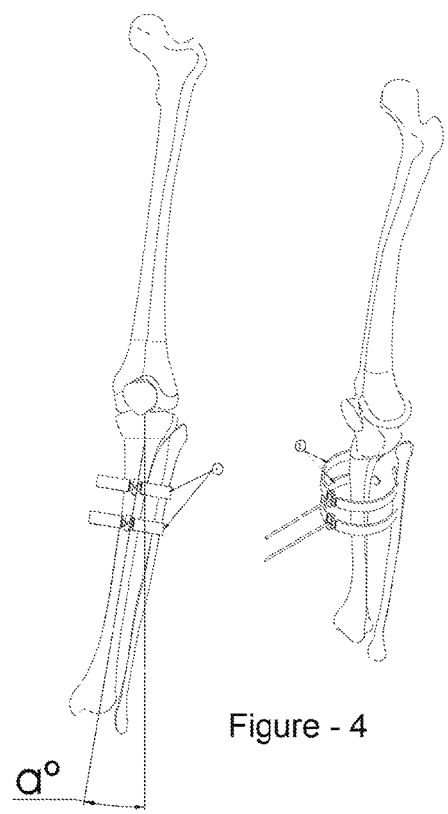
FIG. 4; A representative application of the invention is a drawing showing the aligners which are used to centralize the system to tibia.
Figure 5:
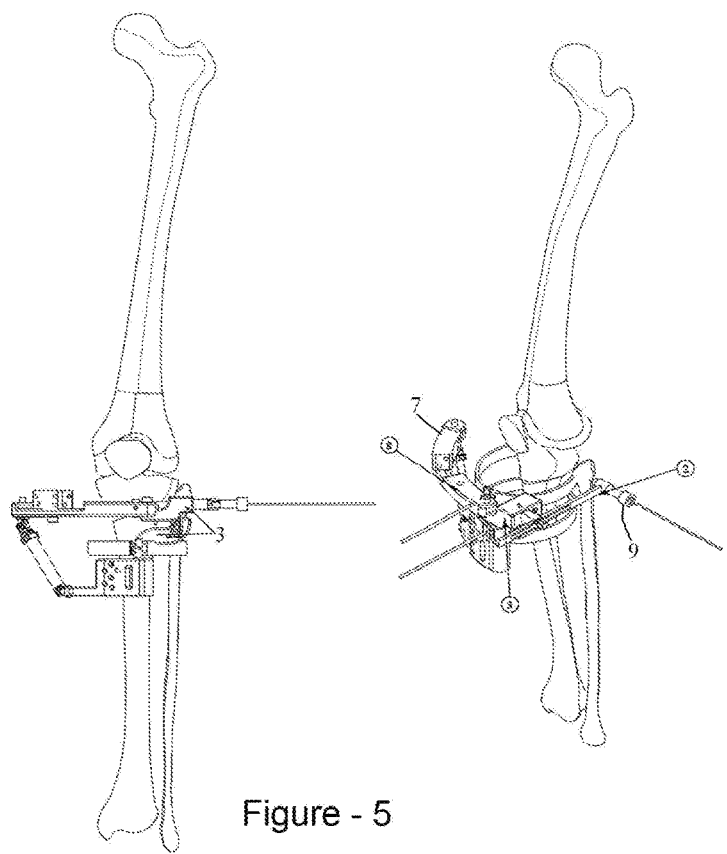
FIG. 5; A representative application of the invention is a drawing showing Fibula head aligner apparatus which is used for the projection of the external fixator to the fibula head.
Figure 6:
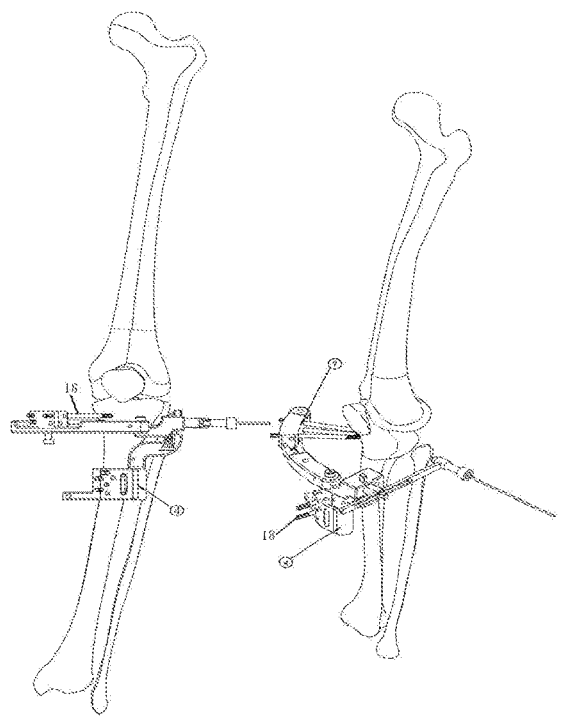
FIG. 6; A representative application of the invention is a drawing showing the sending of the schanz screws from the distal and proximal schanz holders of the external fixator.
Figure 7:
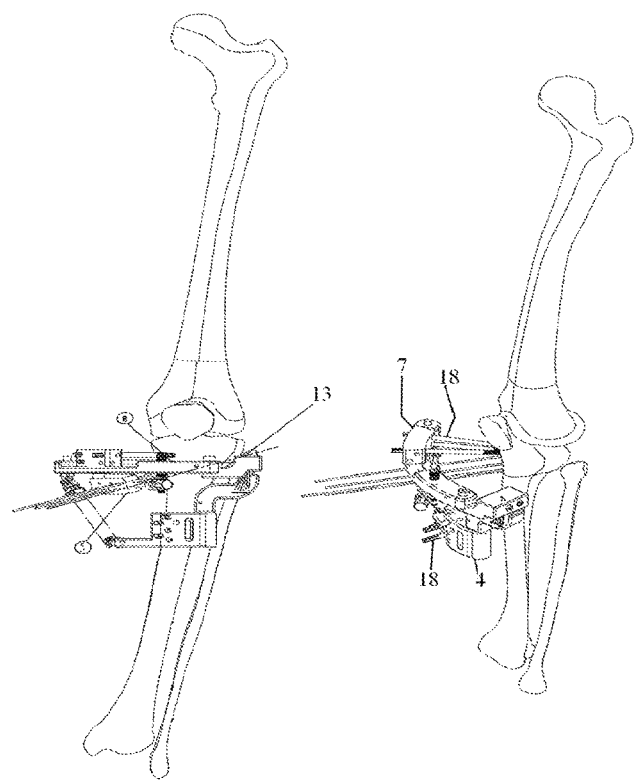
FIG. 7; A representative application of the invention is a drawing showing Kirschner wires sent over the Osteotomy block to the fibula head FIG. 8; A representative application of the invention is a drawing showing the osteotomy block brought closer to the skin over the Kirschner wires FIG. 9; A representative application of the invention is a drawing showing the osteotomy with the surgical bone saw through the osteotomy block FIG. 10; A representative application of the invention is a drawing showing the osteotomy with a manual osteotome.
Figure 8:
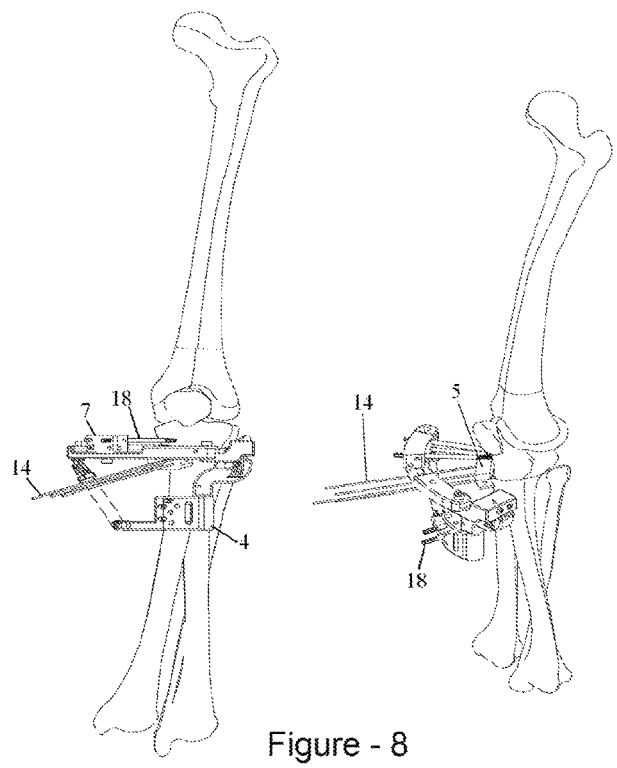
Figure 9:
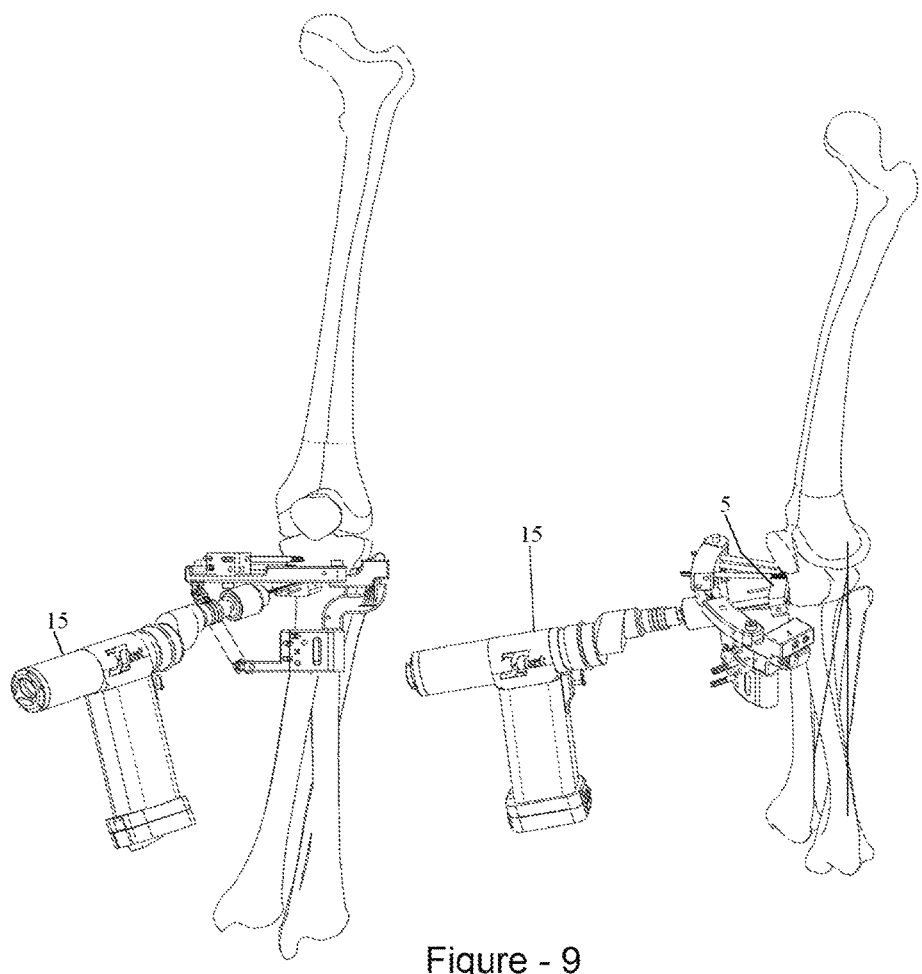
Figure 10:
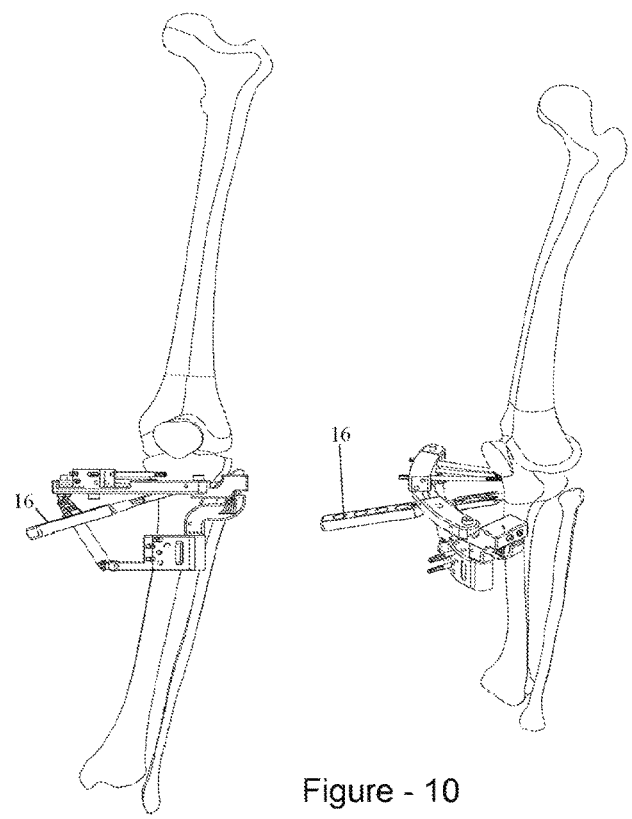
Figure 11:
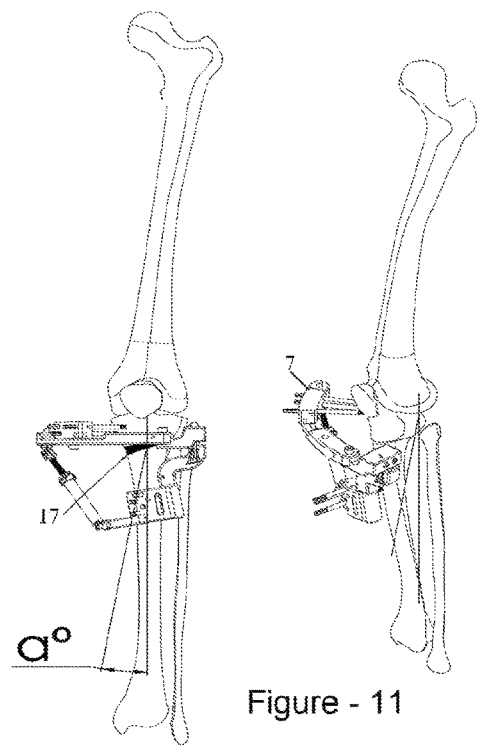
FIG. 11; A representative application of the invention is a drawing showing the placing of the graft after osteotomy and distraction procedure and the final position of the fixator to the tibia.

| | |
|---|---|
| 1 | Positioner |
| 2 | Fibular head positioning device |
| 3 | Angulation Device |
| 4 | Distal schanz holder |
| 5 | Osteotomy Block |
| 6 | Distractor |
| 7 | Proximal Schanz holder |
| 8 | Proximal arch |
| 9 | Fibula Kirschner wire guiding screw |
| 10 | Fibula Kirschner wire guide body |
| 11 | Fibula Kirschner wire guide body connection screw |
| 12 | Fibula Kirschner wire guide connection part |
| 13 | Fibula head |
| 14 | Kirschner wire |
| 15 | Surgical saw |
| 16 | Manual osteotome |
| 17 | Autogenous and/or allogeneic graft |
| 18 | Schanz screw |
| 19 | Angular indicator (scale) |
| 20 | Hinge point |
| 21 | Schanz screw slot |
| 22 | Kirschner wire slot |
| 23 | Osteotomy opening (gap on the osteotomy block) |

DETAILED DESCRIPTION OF A PREFERRED EMBODIMENT

The working principals of our invention of high tibial osteotomy (HTO) external fixator can be explained as follows:

Radiographic images of the knee is taken in a supine position on a radiolucent (ray permeable) table under the control of a fluoroscopy when the patella is in the middle position.

With a proximal arch which is appropriate to the patients cruris proximal (upper part of the leg, just below the knee joint) diameter size, a high tibial osteotomy (HTO) external fixator is installed.

By the set up process angulation device, proximal arch, proximal schanz screw holder, distal schanz screw holder and the distractor is used.

The high tibial osteotomy (HTO) external fixator is centered to anterior tibial cruris (in the middle of the leg) with the Positioner (1)

A high tibial osteotomy (HTO) external fixator is positioned to coronal (frontal or on the front looking position) plan as projection to fibular head (13) with a Fibular head positioning device (2) which is on the Hinge point (20) of the tip of the angulation device (3). The used equipment for positioning the fixator to fibula head are composed of Fibular head positioning device (2); Fibula Kirschner wire guiding screw (9); Fibula Kirschner wire guide body (10); Fibula Kirschner wire guide body connection screw (11); Fibula Kirschner wire guide connection part (12).

The High tibial osteotomy (HTO) external fixator is fixed to the tibia with the schanz screws (18) that are send in desired configuration from the proximal or distal schanz screw holders (7,4).

The osteotomy block (5) is placed to its place on the proximal arch (8). One Kirschner wire (14) is sent through the first hole of the osteotomy block (5) aligned to the tip of the fibula head (13) and the axis of the wire (orientation) is checked by fluoroscopy Once thought to be appropriate at least two more Kirschner wires (14) are sent to the proximal of the tibia and the connection of the osteotomy block (5) to the proximal arch (8) is removed.

The osteotomy block (5) is broad over the Kirschner wires (14) near to the skin and the area of the skin for the incision is determined where the surgical saw (15) is entered over the osteotomy block (5).

After skin and subcutaneous incision, the pes anserinus facia is opened to be parallel to the skin incision and reached to the bone.

The osteotomy is started under the control of fluoroscopy with the surgical saw (15) over the osteotomy block (5). The cut (the medial incision is continued towards the lateral tibia) is continued until it approached 1 cm to the lateral cortex. Afterwards the osteotomy block (5) and the kirschner wires (14) are removed and the osteotomy is continued to cut the anterior and posterior cortex with manual osteotomes (16).

Once the osteotomy is completed the desired correction amount is obtained gradually by looking to the scale (19) with the help of the screws on the hinge point (20). If desired the distractor (6) could be used for this purpose, too.

After enough distraction (angular correction) at the osteotomy site is obtained the system is locked with the help of the screws on the hinge point (20) and the distractor (6). If desired the osteotomy line could be filled with Autogenous and/or allogeneic graft (17).

Indications of High Tibial Osteotomy (HTO) External Fixator are as Follows:
  Genu varum deformities that the mechanical axis is impaired in varus position and unicompartmental osteoarthritis cases,
  When the medial compartment is overloaded after menisectomy,
  In Osteochondral defects with resurfacing arthroplasty applications, The Description in the Scientific Literature for the Requirements of HTO Applications which are Sorted Below, are also Valid for the HTO External Fixator:
  The presence of knee osteoarthritis with involvement of medial compartment
  Lack of inflammatory arthritis in the knee joint,
  When the knee range of motion is over 100°
  The lack of joint laxity in the medial and lateral plan
  Flexion contracture less than 15°
  The absence of the patellofemoral joint osteoarthritis
  Genu varum deformity cases that does not require more than 20° correction
  Body mass index of less than 25

Benefits and Advantages of the High Tibial Osteotomy (HTO) External Fixator is as Follows:
  Proximal arch (8) which is based of carbon fiber and due to the aluminum and titanium based additional components it is very light (the weight varies according to the used schanz screws amount (18) between about 400-450 g)
  The distraction can be occurred without damaging the lateral cortex, because of the projection of the hinge point (20) which has the same projection with the osteotomy line which extends to lateral cortex on the frontal plan.

Owing to the 10° posterior slope on the osteotomy block the tibial slope is regulated automatically (if desired with the motion of the osteotomy block the angle regulation could be changed)

There is a possibility to send schanz screws (18) over the proximal and distal schanz holders (7, 4) in different angles and configurations There is a possibility to make adjustments on the system with the help of the distractor (6).

The Points that Provide Advantages than the Other Implants (Plates, Staples, etc.) are as Follows:

After surgery does not require the application of a plaster-splint.

The patient has the ability to give full weight bearing immediately after surgery.

It has a stable structure that allows early active motion and full weight bearing even if a cortex damage or presence of the plateau fracture occurs during the surgery.

A small skin incision is made for this surgery. In this way there is no need to make large incisions.

In early postoperative period according to the radiographic control, there is a possibility to change the amount of the correction.

There is no need for a second surgery (and anesthesia) for removal of the High tibial osteotomy (HTO) external fixator.

A high tibial osteotomy (HTO) external fixator is created with at least one positioner (1) that is gripping the leg from both side, at least one angulation device (3) and a proximal arch (8) that is connected to the positioner (1), at least one proximal schanz holder (7) on the proximal arch (8), at least one distal schanz holder (4) at the bottom of the angulation device (3), at least one osteotomy block (5) that enables to set the size and the location of the incision on the proximal arch (8) mounted, disassembled, at least one fibular head positioning device (2) that is connected to angulation device (3) and at least one angular indicator (scale) (19) on which the correction could adjust and controlled on the fixator.

It includes one distractor (6) between proximal arch (8) and distal schanz holder (4) that is connected through angulation device (3) with proximal arch (8). At least one schanz screw slot (21) is created on the distal and proximal screw holder (4, 7). There is at least one osteotomy opening (23) in an angled position and/or a Kirschner wire slot (22) on the osteotomy block (5).

It includes at least one hinge point (20) in the end portion of the angulation device (3) that allows angular correction position.

In One Preferred Application Method of the Invention:

The high tibial osteotomy (HTO) external fixator is centered with the positioners (1) to the anterior tibial cruris (on to the middle of the leg), building a high tibial osteotomy external fixator with an appropriate proximal arch (8) which is chosen according to the diameter of the patient's cruris proximal (upper part of the leg, just below the knee joint), proximal schanz holder (7), angulation device (3), distal schanz holder (4) and distractor (6) parts.

positioning the high tibial osteotomy (HTO) external fixator to coronal (frontal or on the front looking position) plan as projection to fibular head (13) with a Fibular head positioning device (2) which is on the Hinge point (20) of the tip of the angulation device (3), while the proximal arch (8) is hold parallel to the proximal tibial join surface (the knee joint line).

fixing the High tibial osteotomy (HTO) external fixator to the tibia with the schanz screws (18) that are send in desired configuration from the proximal or distal schanz screw holders (7,4).

securing the osteotomy block (5) in its place on the proximal arch (8).

sending one Kirschner wire (14) through the first hole of the osteotomy block (5) aligned to the tip of the fibula head (13) and checking the axis of the wire (orientation) by fluoroscopy Once thought to be appropriate sending at least two more Kirschner wires (14) to the proximal of the tibia.

bringing the osteotomy block (5) over the Kirschner wires (14) near to the skin and determining the area of the skin for the incision where the surgical saw (15) is entering over the osteotomy block (5).

reaching to the bone, after skin and subcutaneous incision opening the pes anserinus facia parallel to the skin incision.

beginning the osteotomy under the control of fluoroscopy with the surgical saw (15) over the osteotomy block (5).

continuing the cut (the medial incision is continued towards the lateral tibia) until it approaches 1 cm to the lateral cortex.

Afterwards removing the osteotomy block (5) and the kirschner wires (14) and continuing the osteotomy to cut the anterior and posterior cortex with manual osteotomes (16).

After completing the osteotomy the desired correction amount is obtained gradually by looking to the scale (19) with the help of the screws on the hinge point (20). If desired the distractor (6) can be used for this purpose, too.

After obtaining enough distraction (angular correction) at the osteotomy site the system is locked with the help of the screws on the hinge point (20) and the distractor (6). If desired the osteotomy line can be filled with Autogenous and/or allogeneic graft (17).

The Hinge point (20) which has the same projection with the osteotomy line reaching lateral cortex on the frontal plane, is formed for the realization of the distraction with no damage of the lateral cortex.

Over the osteotomy block (5) which regulates the tibial slope automatically has at least one osteotomy opening (23) with a 10° posterior slope. The fibular head positioning device (2) is composed of Fibula Kirschner wire guiding screw (9), Fibula Kirschner wire guide body (10), Fibula Kirschner wire guide body connection screw (11) and Fibula Kirschner wire guide connection part.

It includes proximal arch (8) which has a slot on which the proximal schanz holder (7) adjust its position by moving. It includes at least one distractor (6) between proximal arch (8) and distal schanz holder (4).

The invention claimed is:

1. An external fixator for use in a high tibial osteotomy (HTO) surgery comprising:
   at least one positioner configured to grip a leg from at least one side;
   at least one angulation device and at least one proximal arch, at least one of the angulation device and the proximal arch being connected to the positioner;
   at least one proximal schanz holder connected to the proximal arch;
   at least one distal schanz holder secured to a bottom of the angulation device;
   at least one osteotomy block that is configured to set the size and the location of an incision on the at least one proximal arch;

at least one fibular head positioning device that is connected to the at least one angulation device; and
at least one angular indicator scale to measure the alignment of the leg as controlled by the external fixator.

2. The external fixator of claim 1 including at least one distractor extending between the at least one proximal arch and the at least one distal schanz holder, the distal schanz holder also being connected indirectly to the at least one proximal arch through the at least one angulation device.

3. The external fixator of claim 2 wherein at least one of the at least one proximal schanz holder and the at least one distal schanz holder includes a schanz screw slot.

4. The external fixator of claim 1 wherein at least one of the at least one proximal schanz holder and the at least one distal schanz holder includes a schanz screw slot.

5. The external fixator of claim 1 wherein the at least one osteotomy block includes at least one osteotomy opening that is oriented in an angled position.

6. The external fixator of claim 5 wherein the at least one osteotomy opening has a 10° posterior slope on the osteotomy block which regulates the tibial slope automatically.

7. The external fixator of claim 1 wherein the at least one osteotomy block includes a Kirschner wire slot.

8. The external fixator of claim 1 wherein the at least one angulation device includes an end portion having at least one hinge point that allows for the correction of an angular position.

9. The external fixator of claim 8 wherein the hinge point has the same projection with the osteotomy line reaching lateral cortex on the frontal plane, for the realization of the distraction with no damage of the lateral cortex.

10. Using the external fixator of claim 1 on a leg of a patient according to the following method:
    securing and centering the at least one positioner to the anterior tibial cruris (the middle of the leg);
    assembling the proximal arch, the proximal schanz holder, the angulation device, the distal schanz holder, and a distractor to form the external fixator, the proximal arch being chosen according to the diameter of the patient's cruris proximal (upper part of leg, just below the knee joint);
    positioning the external fixator in a coronal (frontal or on the front looking position) plane as projection to the patient's fibular head with a fibular head positioning device which is secured to a hinge point on a tip of the angulation device, while the proximal arch is held parallel to the patient's proximal tibial joint surface (the knee joint line);
    fixing the external fixator to the patient's tibia with schanz screws extending in a desired configuration through the proximal schanz holder and the distal schanz holder;
    securing the osteotomy block to the proximal arch;
    passing a Kirschner wire through a first hole of the osteotomy block, the Kirschner wire being aligned to a tip of the patient's fibula head, and checking the axis of orientation of the Kirschner wire by fluoroscopy;
    once the alignment is correct, then passing at least two more Kirschner wires to a proximal of the patient's tibia;
    moving the osteotomy block along the Kirschner wires proximate to the patient's skin, and determining an area of the patient's skin for incision where a surgical saw enters over the osteotomy block;
    cutting an incision through the patient's skin and subcutaneous to the patient's bone and opening the pes anserinus facia parallel to the skin incision;
    beginning the osteotomy under the control of fluoroscopy with the surgical saw over the osteotomy block;
    continuing the cut (the medial incision is continued towards the lateral tibia) until it approaches 1 cm to the lateral cortex;
    removing the osteotomy block and the Kirschner wires, and continuing the osteotomy to cut the anterior and posterior cortex with manual osteotomes;
    verifying that the correct amount of alignment has been created through the osteotomy by viewing the at least one angular indicator scale; and
    once enough distraction (angular correction) has been obtained at the osteotomy site, the external fixator is locked in position using screws on the hinge point and the distractor.

11. The method of using the external fixator according to claim 10 comprising the step of verifying that the correct amount of alignment has been created using the distractor, along with viewing the at least one angular indicator scale.

12. The method of using the external fixator according to claim 10 including the step of filling the osteotomy line with a bodily tissue, such as an autogenous graft or an allogeneic graft.

13. The external fixator of claim 1 including a fibular head positioning device comprising a fibula Kirschner wire guiding screw, a fibula Kirschner wire guide body, a fibula Kirschner wire guide body connection screw, and a fibula Kirschner wire guide connection part.

14. The external fixator of claim 1 wherein the at least one proximal arch has a slot, and the at least one proximal schanz holder is slidably adjustable in position on the proximal arch by moving along the slot.

* * * * *